US010639146B2

(12) United States Patent
Quadri et al.

(10) Patent No.: US 10,639,146 B2
(45) Date of Patent: May 5, 2020

(54) REPLACEMENT HEART VALVE

(71) Applicant: Edwards Lifesciences CardiAQ LLC, Irvine, CA (US)

(72) Inventors: Arshad Quadri, West Hartford, CT (US); J. Brent Ratz, Winchester, MA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 15/415,794

(22) Filed: Jan. 25, 2017

(65) Prior Publication Data

US 2017/0354496 A1 Dec. 14, 2017

Related U.S. Application Data

(63) Continuation of application No. 13/165,721, filed on Jun. 21, 2011, now abandoned.

(60) Provisional application No. 61/357,048, filed on Jun. 21, 2010.

(51) Int. Cl.
*A61F 2/24* (2006.01)

(52) U.S. Cl.
CPC .......... *A61F 2/2418* (2013.01); *A61F 2/2415* (2013.01); *A61F 2220/0008* (2013.01); *A61F 2230/008* (2013.01); *A61F 2230/0054* (2013.01); *A61F 2230/0067* (2013.01); *A61F 2250/0029* (2013.01); *A61F 2250/0039* (2013.01)

(58) Field of Classification Search
None
See application file for complete search history.

(56) References Cited

U.S. PATENT DOCUMENTS

| 3,657,744 | A | 4/1972 | Ersek |
| 3,671,979 | A | 6/1972 | Moulopoulos |
| 3,739,402 | A | 6/1973 | Cooley et al. |
| 4,056,854 | A | 11/1977 | Boretos et al. |
| 4,079,468 | A | 3/1978 | Liotta et al. |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

(Continued)

*Primary Examiner* — Leslie Lopez
(74) *Attorney, Agent, or Firm* — Knobbe Martens Olson & Bear LLP

(57) ABSTRACT

A replacement heart valve can have an expandable frame configured to engage a native valve annulus. A valve body can be mounted onto the expandable frame to provide functionality similar to a natural valve. The valve body has an upstream end and a downstream end, and a diameter at the downstream end is greater than a diameter at the upstream end.

17 Claims, 14 Drawing Sheets

(56) References Cited

U.S. PATENT DOCUMENTS

| | | |
|---|---|---|
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | DiMatteo et al. |
| 6,458,153 B1 | 10/2002 | Bailey et al. |
| 6,482,228 B1 | 11/2002 | Norred |
| 6,511,491 B2 | 1/2003 | Grudem et al. |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,629,534 B1 | 10/2003 | St Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,252,682 B2 | 8/2007 | Seguin |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,673,000 B2 | 3/2014 | Tabor et al. |

(56) References Cited

U.S. PATENT DOCUMENTS

| | | |
|---|---|---|
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |

(56) References Cited

U.S. PATENT DOCUMENTS

| | | |
|---|---|---|
| 2008/0071361 A1* | 3/2008 | Tuval .......... A61F 2/2418 623/2.1 |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0082094 A1 | 4/2010 | Quadri et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |

(56) References Cited

U.S. PATENT DOCUMENTS

| | | |
|---|---|---|
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1259194 B1 | 11/2002 |
| EP | 1281375 B1 | 2/2003 |
| EP | 1369098 A1 | 12/2003 |
| EP | 1472996 A1 | 11/2004 |
| EP | 1734903 A1 | 12/2006 |
| EP | 1255510 B1 | 4/2007 |
| EP | 1827558 A2 | 9/2007 |
| EP | 1239901 B1 | 10/2007 |
| EP | 2124826 B1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 B1 | 5/2011 |
| EP | 2398543 A1 | 12/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2926766 B1 | 10/2015 |
| EP | 2967858 A2 | 1/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 1997049355 A1 | 12/1997 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | WO-2007058857 A2 * | 5/2007 ........... A61F 2/2418 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009042196 A2 | 4/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. 2010.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. 2006.

(56) References Cited

OTHER PUBLICATIONS

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.
Spillner, J. et al., "New Sutureless 'Atrial- Mitral-Valve Prosthesis' for Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.
Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.
Seidel, Wolfgang, et al., "A Mitral Valve Prosthesis and a Study of Thrombosis on Heart Valves in Dogs," JSR—vol. II, No. 3—May, 1962, submitted for publication Oct. 9, 1961.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
CardiAQ Valve Technologies, "Innovations in Heart Valve Therapy," In3 San Francisco, Jun. 18, 2008, PowerPoint presentation in 19 slides.
Ratz, J. Brent, "LSI EMT Spotlight," May 15, 2009.
Ratz, J. Brent, "In3 Company Overview," Jun. 24, 2009.
"Company Overview," at TVT on Jun. 25, 2009.
Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May 2011 at TVT.

Mack, Michael, M.D., "Antegrade Transcatheter Mitral valve Implantation: On-Going Experience in Swine Model," Applicant believes this may have been presented on Nov. 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (An Acute In Vivo Study)," Applicant believes his may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/hrcardio/journal/v11/n3/full/nrcardio.2013.221.html?message-global=remove#access. Jan. 21, 2014.
Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve" Contemporary Reviews in Interventional Cardiology, Circ. Cardiovasc. Intervent., 2008;1:74-81, Applicant believes this may have been available as early as Aug. 2008.
Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Dave Fornell, "Transcatheter Mitral Valve replacement Devices in Development," Diagnostic and Interventional cardiology, Dec. 30,

(56) References Cited

OTHER PUBLICATIONS 2014, p. 3, <http://www.dicardiology.com/article/transcatheter-mitral-valve-replacement-devices-development>.

The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Neovasc corporate presentation, Oct. 2009, available at http://www.neovasc.com/investors/documents/Neovasc-Corporate-Presentation-October-2009.pdf.

NJ350: Vote for Your Favorite New Jersey Innovations, Jun. 27, 2014, http://www.kilmerhouse.com/2014/06/nj350-vote-for-your-favorite-new-jersey-innovations/.

\* cited by examiner

REPLACEMENT HEART VALVE

CROSS-REFERENCE TO RELATED APPLICATIONS

This application is a continuation of U.S. application Ser. No. 13/165,721, filed Jun. 21, 2011, which claims priority to U.S. Provisional Application No. 61/357,048, which was filed on Jun. 21, 2010. The entire contents of the above applications are hereby incorporated by reference herein. Further, Applicants' U.S. application Ser. No. 12/569,856, filed Sep. 29, 2009, and U.S. application Ser. No. 12/761,349, filed Apr. 15, 2010 disclose several embodiments of replacement heart valves. In some instances the present disclosure describes embodiments and principles that build upon and improve embodiments disclosed in these previous applications. As such, the entirety of each of these prior applications is incorporated by reference into this disclosure.

BACKGROUND

Field of the Invention

The present invention relates generally to replacement heart valves.

Description of Related Art

Human heart valves, which include the aortic, pulmonary, mitral and tricuspid valves, function essentially as one-way valves operating in synchronization with the pumping heart. The valves allow blood to flow in a downstream direction, but block blood from flowing in an upstream direction. Diseased heart valves exhibit impairments such as narrowing of the valve or regurgitation. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatus to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves, that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of replacement heart valves that can be compacted for delivery and then controllably expanded for controlled placement has proven to be particularly challenging.

SUMMARY OF THE INVENTION

Accordingly, there is in the need of the art for an improved replacement heart valve.

In accordance with one embodiment, the present invention provides a replacement heart valve that comprises an expandable frame and a valve body mounted onto the expandable frame. The expandable frame may have an engagement system configured to engage a native valve annulus at an engagement zone along the length of the frame. The frame can have an upstream portion, a downstream portion, and a transition portion between the upstream and downstream portions, where a diameter of the downstream portion is greater than a diameter of the upstream portion. The valve body can have a plurality of valve leaflets configured to move between an open condition and a closed condition. A diameter of the valve body at a downstream end of the leaflets can be greater than a diameter of the valve body at an upstream end of the leaflets and the upstream end of each leaflet can be positioned upstream of the frame engagement zone.

In some embodiments, the engagement system comprises a set of upstream anchors and a set of downstream anchors, each anchor comprising an anchor tip, and the frame engagement zone is defined between the tips of the upstream and downstream anchors.

The anchors can include one of many features. For example, a diameter defined by the tips of the upstream anchors can be approximately equal to a diameter defined by the tips of the downstream anchors. As another example, the downstream anchors can extend from the downstream portion of the expandable frame and the upstream anchors can extend from an area of the frame having a diameter less than the downstream portion, such as the upstream portion or the transition portion of the expandable frame.

In some embodiments, a replacement heart valve comprises an expandable frame configured to engage a native valve annulus at an engagement zone along the length of the frame and a valve body attached to the expandable frame. The expandable frame can include a foreshortening portion configured to longitudinally contract as the frame radially expands from a compacted to an expanded condition, a plurality of first anchors and a plurality of second anchors.

Each of the anchors, according to some embodiments, can extend radially outwardly from the frame at an anchor base and terminate at an anchor tip. At least part of the foreshortening portion can be disposed between the first and second anchor bases and the engagement zone can be defined between the first and second anchor tips. Further, the first anchors can comprise first, second and third spaced apart bending stages along the length of each upstream anchor, and wherein the first anchor is bent radially outwardly in the first and second bending stages, and is bent in an opposite direction in the third bending stage.

The anchors may include additional features. For example, the portion of the first anchor between the third bending stage and the anchor tip can be generally parallel to an axis of the frame. The second anchor can comprise first, second and third spaced apart bending stages, and wherein in the first bending stage the anchor is bent radially inwardly, in the second bending stage the anchor is bent radially outwardly, and in the third bending stage the anchor is bent radially inwardly. The second bending stage of the first anchor can be bent about 180 degrees.

According to some embodiments, a replacement heart valve comprises an expandable frame configured to engage a native valve annulus at an engagement zone along the length of the frame, and a valve body attached to the expandable frame. The valve body can comprise a plurality of valve leaflets configured to open to allow flow in a first direction and engage one another so as to close and not allow flow in a second direction opposite the first direction. The expandable frame can comprise an upstream portion, a downstream portion, a transition portion, a plurality of upstream anchors and a plurality of downstream anchors.

The downstream portion can have a diameter different than a diameter of the upstream portion. The transition portion can be between the upstream and downstream portions. Each anchor can extend radially outwardly from the frame at an anchor base and terminate at an anchor tip. At least part of a foreshortening portion disposed between the upstream and downstream anchor bases. The engagement zone defined between the upstream and downstream anchor tips. The bases of the upstream anchors can be disposed at a location along the length of the frame having a first diameter, and the bases of the downstream anchors can be disposed at a location along the length of the frame having a second diameter, and the first diameter is different than the second diameter.

In some embodiments, the diameter of the downstream portion is greater than the diameter of the upstream portion. In addition, in some embodiments, the bases of the upstream anchors are disposed in the upstream portion, and the bases of the downstream anchors are disposed in the downstream portion or the bases of the upstream anchors are disposed in the transition portion, and the bases of the downstream anchors are disposed in the downstream portion.

In some embodiments, a replacement heart valve comprises an expandable frame configured to engage a native valve annulus and a valve body mounted onto the expandable frame. The valve body can comprise a plurality of valve leaflets configured to open to allow flow in a first direction and engage one another so as to close and not allow flow in a second direction opposite the first direction. The valve body can have an upstream end and a downstream end where a diameter at the downstream end is greater than a diameter at the upstream end.

In some embodiments, a replacement heart valve comprises an expandable frame configured to engage a native valve annulus and a valve body mounted onto the expandable frame. The valve body can include a plurality of valve leaflets configured to open to allow flow in a first direction and engage one another so as to close and not allow flow in a second direction opposite the first direction. The expandable frame can have an upstream portion, a downstream portion, a first set of anchors, and a second set of anchors. A diameter of the expandable frame at the downstream portion can be greater than a diameter of the expandable frame at the upstream portion. Further, each anchor can comprise an anchor tip. The first set of anchors can extend from the downstream portion of the expandable frame and the second set of anchors can extend from an area of the frame having a diameter less than the downstream portion. The anchor tips of the first set of anchors can be configured to be positioned generally opposed to the anchor tips of the second set of anchors when the expandable frame is engaged to the native valve annulus.

Other inventive embodiments and features are disclosed below.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIG. 15 is an image, from the perspective of the left ventricle, of one embodiment of a replacement heart valve positioned within a native mitral valve.

FIG. 16 is another image, from the perspective of the left ventricle, of the replacement heart valve of FIG. 15 positioned within a native mitral valve.

FIG. 17 is another image, from the perspective of the left ventricle, of the replacement heart valve of FIG. 15 positioned within a native mitral valve.

FIG. 18 is an image, from the perspective of the left atrium, of the replacement heart valve of FIG. 15 positioned within a native mitral valve.

FIG. 19 is an image, from the perspective of the left atrium, of the replacement heart valve of FIG. 15 positioned within a native mitral valve.

DETAILED DESCRIPTION OF PREFERRED EMBODIMENTS

The present specification and drawings disclose aspects and features of the invention in the context of several embodiments of replacement heart valves and portions thereof that are configured for replacement of natural heart valves in a patient. These embodiments may be discussed in connection with replacing specific valves such as the patient's aortic or mitral valve. However, it is to be understood that the context of a particular valve or particular features of a valve should not be taken as limiting, and features of any one embodiment discussed herein can be combined with features of other embodiments as desired and when appropriate.

Figure 1:
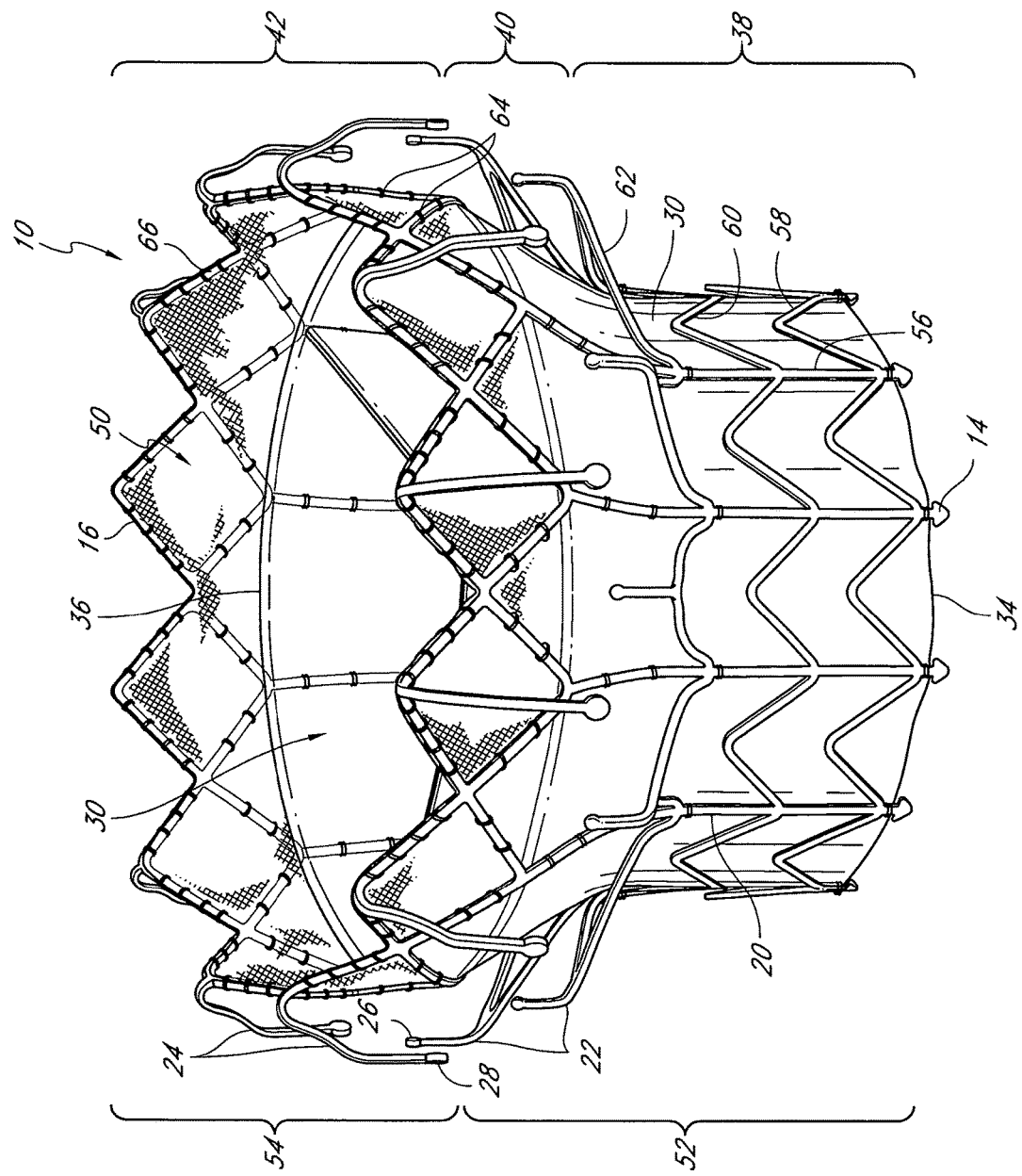
FIG. 1 is a perspective view of one embodiment of a replacement heart valve.
Figure 2:
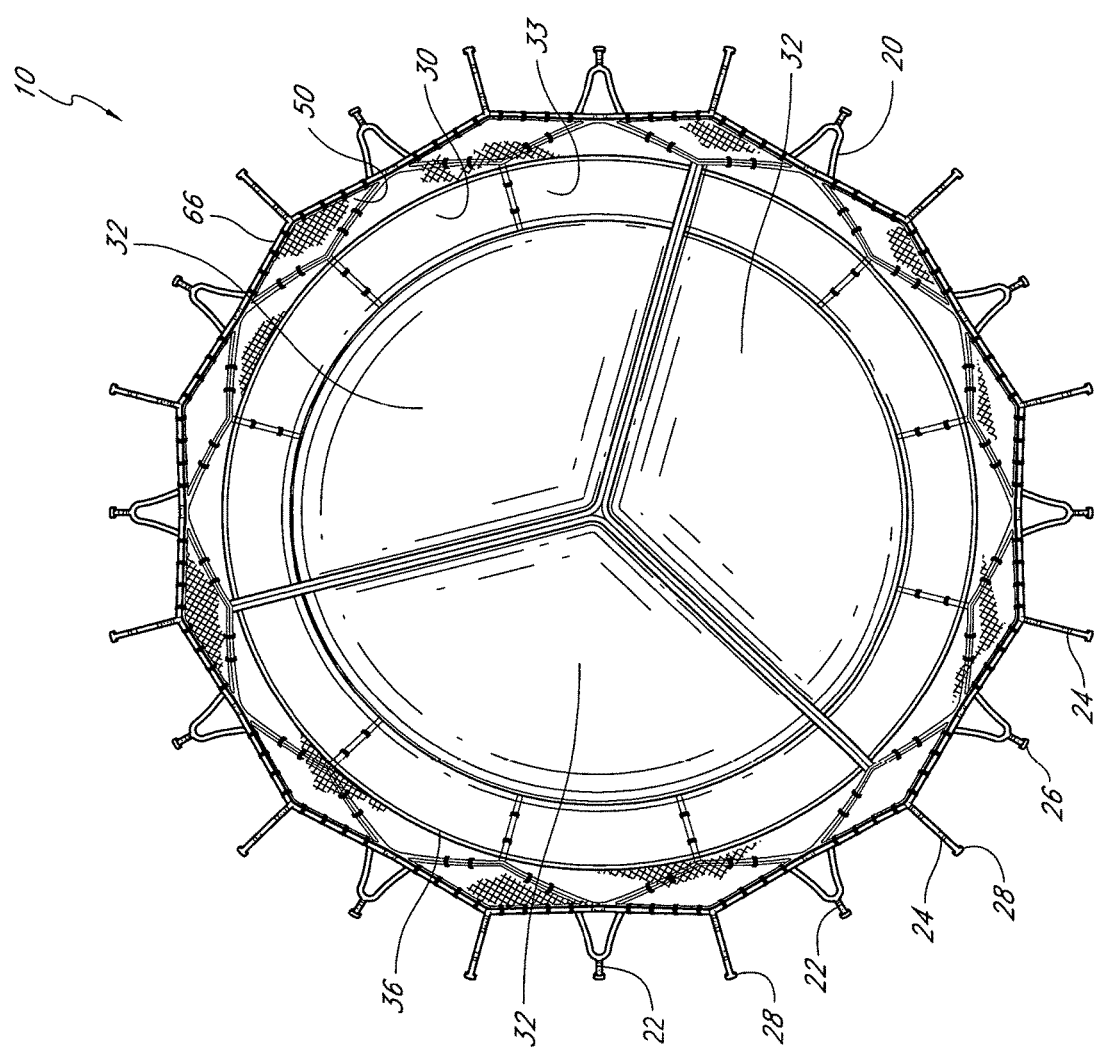
FIG. 2 is a view looking upstream through the replacement heart valve of FIG. 1.

With initial reference to FIGS. 1 and 2, an embodiment of a replacement heart valve 10 is shown. The illustrated replacement heart valve 10 is designed to replace a diseased native mitral valve. In this embodiment, the replacement heart valve 10 is made up of a self-expanding frame 20 to which a valve body 30 is attached. As best seen in FIG. 2, the valve body 30 includes flexible leaflets 32 that open and close. The valve body 30 can include two, three or more leaflets 32. The valve body 30 has an inflow end 34 and an outflow end 36. The replacement heart valve 10 is shown with an upstream portion 38, a transition portion 40 adjacent the upstream portion 38 and a downstream portion 42 disposed adjacent the other side of the transition portion 40.

The valve body 30 can extend the length of the frame 20 or it can extend along only part of the length of the frame 20. For example, the valve body 30 shown in FIGS. 1 and 2 extends along the upstream portion 38 and the transition portion 40. The valve body 30 also extends along the non-foreshortening zone 52. In another embodiment the valve body 30 also extends along the downstream portion 42 and/or the foreshortening zone 54. As shown, in the illustrated embodiment a connection skirt 50 extends along the length of the downstream portion 42. In some embodiments, the ends 14, 16 of the replacement heart valve 10 can coincide with the inflow end 34 of the valve body 30 and the outflow end 36 of the valve body. In the illustrated embodiment, the inflow end 34 substantially coincides with one end 14 of the replacement heart valve 10 while the other end 16 of the replacement heart valve 10 extends past the outflow end 36 of the valve body.

The valve body 30 can be implanted within a heart to replace a damaged or diseased heart valve such as a mitral valve. The valve leaflets 32 can function in a manner similar to the natural mitral valve. For example, a plurality of valve leaflets 32 can open to allow flow in a first direction and engage one another so as to close and not allow flow in a second direction opposite the first direction. The replacement heart valve 10 can be constructed so as the open naturally with the beating of the heart.

Additional example replacement heart valves with valve bodies and leaflets are discussed in detail in Applicants' U.S. application Ser. No. 12/569,856, filed Sep. 29, 2009, incorporated by reference herein in its entirety and with particular reference to FIGS. 1-3C, 5-13 and 17-25 and the accompanying discussion including paragraphs [0063]-[0070], [0083]-[0101], [0110]-[0114], [0118], [0124]-[0128], and [0130]-[0137].

With continued reference to FIGS. 1-2, in this embodiment, the frame 20 is elongate with different diameter sections. For example, the upstream end 14 of replacement heart valve 10 or frame 20 has a first diameter that is substantially less than a second diameter at the downstream end 16. The frame 20 maintains the first diameter along its length in the upstream portion 38. In the transition portion 40 between the upstream 38 and downstream 42 portions, the frame 20 flares outwardly so that the diameter increases to the second diameter. The downstream portion 42 disposed adjacent the transition portion 40 preferably maintains the second diameter along its length.

The frame 20 is constructed from a metal tube, such as a nitinol tube. As such, the frame 20 can be expanded and/or compressed and/or otherwise worked to have the desired introduction and implantation configurations.

The frame 20 is constructed so that part of the frame foreshortens as the frame is radially expanded from a collapsed configuration. In the illustrated embodiment a foreshortening zone 54 generally corresponds with the downstream portion 42. A non-foreshortening zone 52 extends upstream from the foreshortening zone 54, and generally corresponds to the upstream 38 and transition 40 portions.

Opposing anchors 22, 24 are constructed on the frame 20 so that preferably their tips 26, 28 are in the downstream portion 42. The anchors 22, 24 are configured to grasp opposite sides of the native mitral annulus. In some embodiments, one or more of the anchor tips 26, 28 are in the downstream portion 42, the upstream portion 38, the transition portion 40, or at or near the border of the transition portion 40 and the downstream portion 42 or the border of the transition portion 40 and the upstream portion 38.

Preferably, each of the anchors 22, 24 also extends generally radially outwardly from the frame 20 so that the anchor tips 26, 28 are generally spaced away from the rest of the frame 20. In some embodiments, all or part of the structure connected to the anchor tip and extending radially from the frame, including one or more rings and/or struts, can be considered part of the anchor. The anchors can include a base located on the anchor on a side opposite the tip. The base can be for example where the anchor begins to extend away from the frame 20.

As shown, the anchors 22 extend from the downstream portion 42 of the frame 20. For example, the anchors 22 can extend from the end 16 of the frame 20. In some embodiments the anchors 22 can extend from other parts of the downstream portion 42 of the frame. The illustrated anchors 24 extend from the upstream portion 38 of the frame 20. As such, the anchors 24 and the anchors 22 both extend from regions having different diameters. As an additional example, the anchors 24 can extend from the downstream portion 42 and the anchors 22 can extend from the transition portion 40. Alternatively, both set of anchors 22, 24 can extend from the transition portion 40.

The anchors 22, 24 can also extend from regions having the same diameter. For example both sets of anchors can extend from the downstream portion 42.

The anchors 22, 24 can be one of many different lengths. For example, the anchors can be shorter than, as long as or longer than any of the upstream 38, transition 40, and downstream 42 portions. As shown, the anchors 24 are shorter than the downstream portion 42 and the anchors 22 are longer than the transition portion 40. The anchors 22 extend from the upstream portion 38, through the transition portion 40 and into the downstream portion 42. Other configurations are also possible.

The anchor tips 26, 28 can have one of many shapes. For example, the shape can be configured to increase the amount of surface area of the tip that is in contact with tissue. The tips 26, 28 are shown as round or elliptical disks but can have other shapes as well, such as tear drop, rectangular, rectangular with a curved end, etc.

In preferred embodiments, the replacement heart valve 10 may be deployed into a heart valve annulus, and positioned when compacted so that the anchor tips 26, 28 of the opposing anchors 22, 24 are disposed on opposite sides of the native annulus. As the replacement heart valve 10 is expanded, the opposing anchors are drawn closer together so as to grasp opposite sides of the native annulus with the anchor tips 26, 28 and securely hold the replacement heart valve 10 in position. As such, the replacement heart valve 10 can be held securely in position without requiring a substantial radial force against the native annulus. The foreshortening zone 54 can be used to move the anchor tips 26, 28 closer together as the replacement heart valve 10 moves to the expanded position to thereby engage the native valve annulus.

Applicant's U.S. patent application Ser. No. 12/084,586, which was published on Aug. 27, 2009 as U.S. Publication No. 2009/0216314, discusses embodiments of foreshortening stents with anchors, and can be referred to for further discussion of certain aspects of the illustrated embodiments. The above application is incorporated in its entirety by reference herein with particular reference to the discussion concerning structure and operation of embodiments of a foreshortening stent, particularly a foreshortening stent having anchors.

Figure 3A:
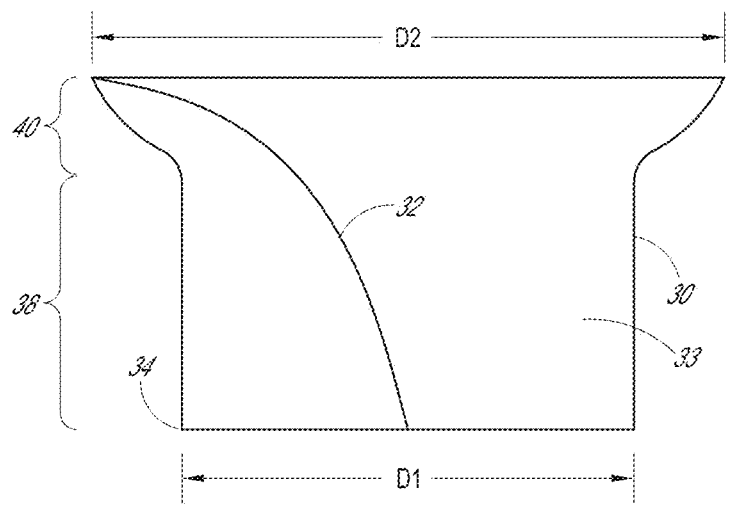
FIGS. 3A and 3B are schematic views of one embodiment of a valve body.
Figure 3B:
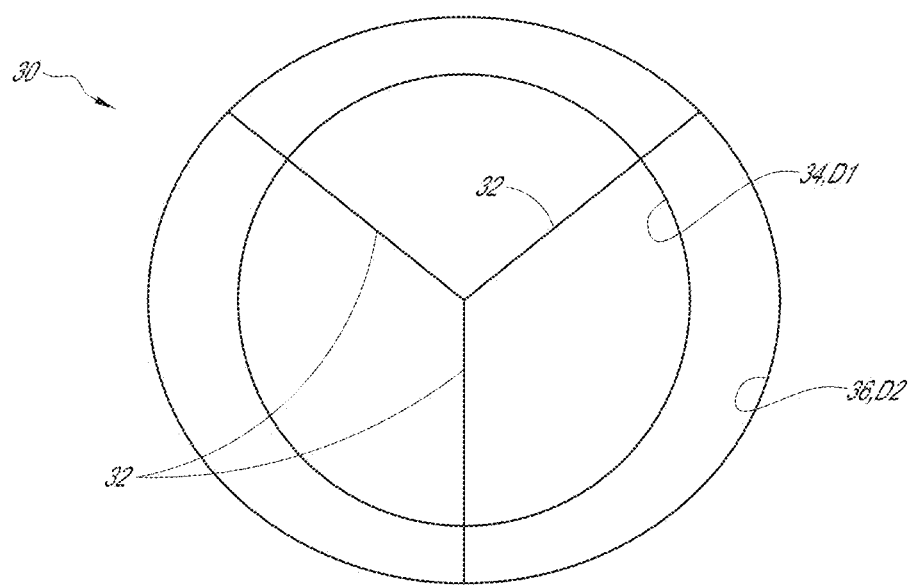

FIGS. 3A-B show an embodiment of the valve body 30 separate from the other components of the replacement heart valve 10. The valve body 30 preferably is shaped to accommodate the transition portion 40 of the frame 20. More specifically, the valve body transition portion 40 is generally conical, where the upstream portion 38 is generally cylindrical. In embodiments where the valve body 30 extends into the downstream portion 42, the downstream portion can also be generally cylindrical. In some embodiments, one or more of the upstream portion 38 and the downstream portion 42 can be generally conical. In the illustrated embodiment, the upstream portion 38 of the valve body 30 has an inflow diameter $D_1$. A downstream, or outflow end 36 of the valve body 30 has a diameter $D_2$ that is greater than the upstream portion diameter $D_1$. Approaching the outflow end 36 of the valve body 30, the valve body flares outwardly to the larger diameter. As such, the inflow diameter $D_1$ of the valve body 30 is less than the outflow diameter $D_2$ of the valve body 30. The inflow $D_1$ and outflow $D_2$ diameters can vary greatly, in some embodiments, the inflow diameter $D_1$ can be approximately 30 mm and the outflow diameter $D_2$ can be approximately 40 mm.

The valve leaflets 32 extend along all or part of the length of the valve body 30, and including all or part of the reduced and increasing diameter portions of the valve body, i.e. the upstream 38 and transition 40 portions, as shown. In some embodiments, the leaflets 32 can also span all or part of the length of the downstream portion 42.

As best shown in FIGS. 1 and 2, the replacement heart valve 10 can also include a connection skirt 50. The connection skirt 50 can be a flexible fabric, preferably a knit polyester fabric. The connection skirt 50 can be attached to one or both of the frame 20 and the valve body 30. As shown, the connection skirt 50 is attached to the distal end of the valve body 30 and also attached to the frame 20 in the foreshortening zone. In the illustrated embodiment, the valve body 30 is attached to the frame 20 so that it is contained within the non-foreshortening zone. In other embodiments, the valve body 30 may be partially contained in both the non-foreshortening zone 52 and the foreshortening zone 54. Some embodiments may not include the connection skirt 50.

Figure 4:
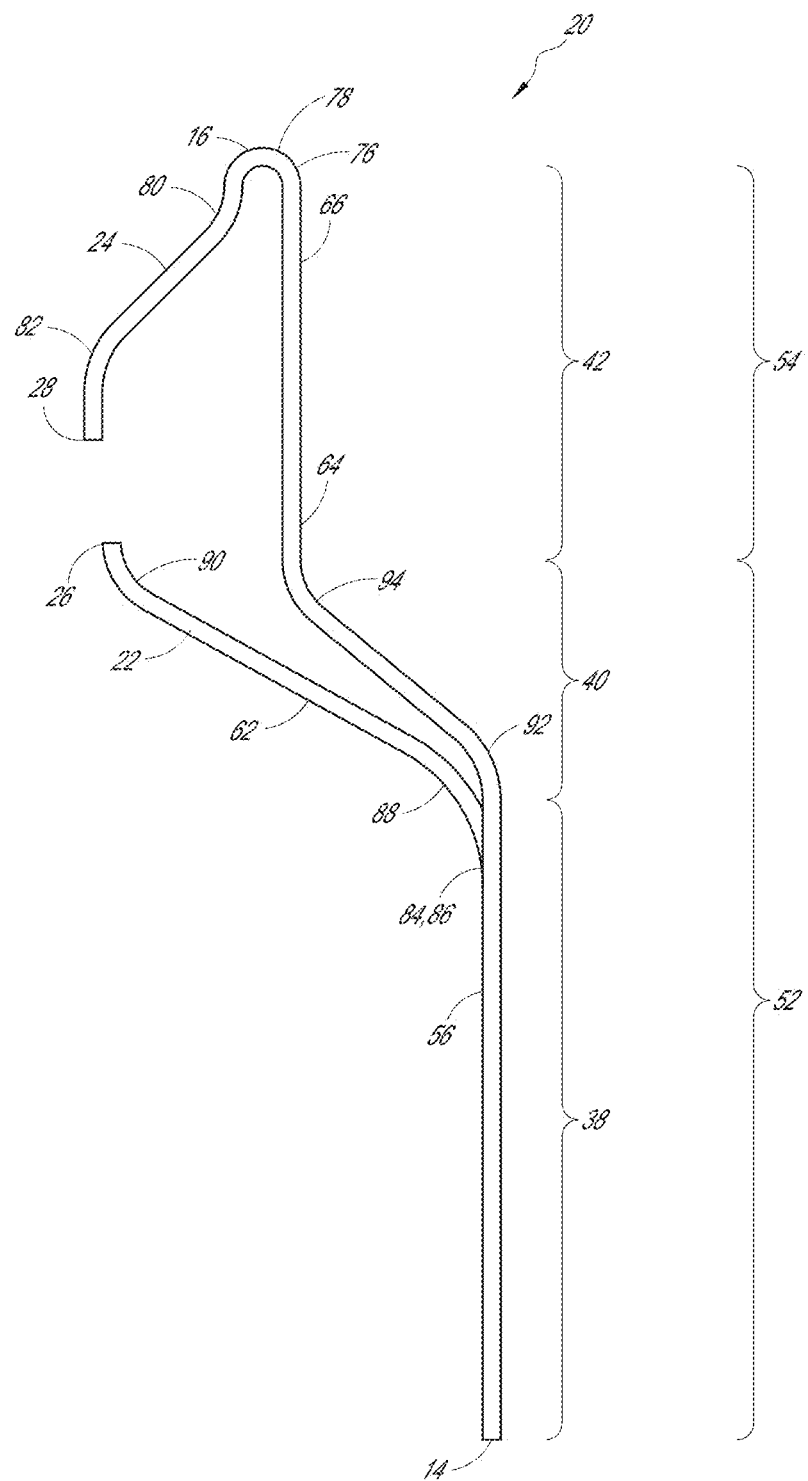
FIG. 4 is a schematic side view of one embodiment of a frame for supporting a valve body.
Figure 5:
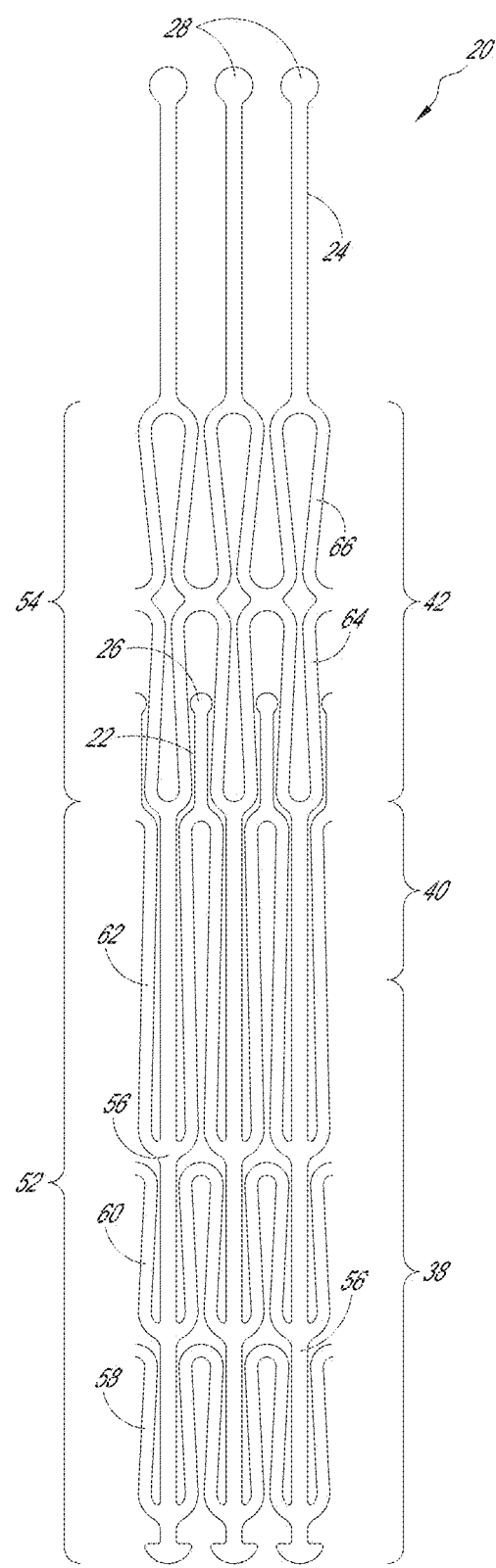
FIG. 5 is a partial flat pattern depiction of the pattern from which the frame of FIG. 4 is cut.

With additional reference to FIGS. 4 and 5, a schematic side view of the frame 20 is shown, along with a flat pattern depiction of the pattern from which the frame 20 is cut from a metal tube, such as a nitinol tube. As mentioned previously, the frame 20 has a non-foreshortening zone 52 and a foreshortening zone 54. As shown, longitudinal struts 56 span the length of the non-foreshortening zone 52. Distal or downstream portions of the longitudinal struts 56 make up the transition portion 40, in which the struts 56 bend so as to flare radially outwardly and then bend again so as to stop expanding in radius and attach to the foreshortening zone 54 of the frame 20. As such, the frame 20 is generally divided into an upstream portion 38 made up of the first diameter, a transition portion 40 at which the diameter is expanding, and a downstream portion 42 which includes the foreshortening zone 54 and which is adapted to engage the native valve annulus.

First 58, second 60, and third 62 rings made up of undulating struts are connected to the longitudinal struts 56 in the non-foreshortening zone 52. The illustrated first 58 and second 60 rings are of generally the same size, however, the struts in the third ring 62 are substantially larger and longer than the struts in the first 58 and second 60 rings. For example, the struts of the first 58 and second 60 rings can be about twice as long as the struts of the third ring 62, or longer. Additionally, upstream anchors 22 extend from the free apices of the struts in the third ring 62. As best shown in FIG. 4, the struts in the third ring 62 preferably are flared radially out at a more dramatic angle than is the longitudinal strut 56 at the transition portion 40. In the illustrated embodiment, the third ring struts 62 can be considered part of the upstream anchors 22.

Referring to FIGS. 4 and 5, a fourth ring 64 is attached to the distal end of the longitudinal struts 56 at an apex of the fourth ring 64. A fifth ring 66 attaches to the fourth ring 66 on the side opposite the longitudinal struts 56. The fifth ring 66 can be a mirror image of the fourth ring 64. As illustrated, the fourth 64 and fifth 66 rings are of generally the same size. The fourth 64 and fifth 66 rings are made up of undulating struts and make up the foreshortening zone 54. Expansion of the replacement heart valve 10 causes the struts of the fourth ring 64 to move farther apart such that they are at a greater angle relative to one another. Thus, they move from a relatively vertical orientation to a more horizontal orientation. This also causes the ring to shrink in vertical height. The fifth ring exhibits similar behavior when the valve 10 expands. This movement of the fourth 64 and fifth 66 rings results in foreshortening of the frame 20.

Additionally, downstream anchors 24 extend from the free apices of the fifth ring 66. As best shown in FIG. 4, the downstream anchors 24 are bent down and flared radially out from the struts of the fourth 64 and fifth 66 rings. The upstream anchors 22 on the third ring 62 are bent so as to generally oppose the downstream anchors 24 that extend from the foreshortening zone 54. A tip 26 of each upstream anchor 22 is downstream of the transition portion 40. As such, the downstream anchors 24 extend from the distal or outflow end 16 of the valve 10, and the upstream anchors 22 extend outwardly from the upstream portion of the valve 10, upstream of the transition portion 40.

The shape of each of the anchors will now be described in more detail with reference to FIG. 4. Each anchor 22, 24 can have one or more bending stages to position the anchor tip in the desired location. Preferably, each anchor has at least two bending stages.

The downstream anchor 24 has a base 76 that is connected to a free apex of the fifth ring 66. After the base 76 there is a first bending stage 78 so that the anchor is radially spaced outwardly from the frame 20. As shown, the anchor at the first bending stage 78 is bent approximately 180 degrees. A large bend such as a bend of approximately 180 degrees, or between around 150-200 degrees, can provide structural support and strength to the anchor. Such a large bend can also be located at other points in the anchor and at other bending stages. A second bending stage 80 is shown used to flare the anchor radially outwardly from the frame 20. In a third bending stage 82 the anchor bends in a radially inward direction so as to direct the anchor tip 28 towards the opposing anchor 22 and position the portion of the anchor between the tip and the third bending stage parallel or substantially parallel to the frame 20. In some embodiments more or fewer bending stages can be used. In addition, the various bending stages can be used to different purposes and to provide different positions of the anchor than those described above.

The upstream anchor 22 can also have one or more bending stages. The anchor 22 has a base 84 where the strut of the third ring 62 connects to the longitudinal strut 56. A first bending stage 86 of the anchor 22 can be located at the base to move the anchor 22 radially outwardly from frame 20. A second bending stage 88 can further move the anchor 22 radially outwardly from frame 20. In this way, the anchor 22 can be bent in a gradual manner away from the frame 20. In some embodiments, one bending stage can be used to move the anchor 22 away from the frame. The anchor 22 can also include a large bend similar to the approximately 180 degree bend in the first bending stage 78 of anchor 24. Finally, anchor 22 is also shown with a third bending stage 90. The third bending stage 90 can direct the anchor tip 26 towards the opposing anchor 24 and position the tip parallel or substantially parallel to the frame 20.

The transition portion 40 can also include one or more bending stages, such as bending stages 92, 94 shown in FIG. 4.

Notably, in this embodiment the native annulus which is intended to be gripped between the anchor tips 26, 28 will be engaged by the foreshortening zone 54 of the frame 20, and will not engage the transition portion 40 of the frame 20. Rather, in a mitral placement, the upstream 38 and transition 40 portions of the replacement valve 10 will not necessarily be disposed within the annulus but mostly or entirely in the atrium.

In the embodiment illustrated in connection with FIGS. 1-5, the valve body 30 is a two-layer valve comprising an outer valve skirt 33 and inner leaflets 32 (see FIGS. 2 and 3A). The outer valve skirt 33 is disposed between the leaflets 32 and the frame 20. It is to be understood, however, that in other embodiments, a single-layer valve body 30 not having an outer valve skirt 33 may be employed.

Figure 6:
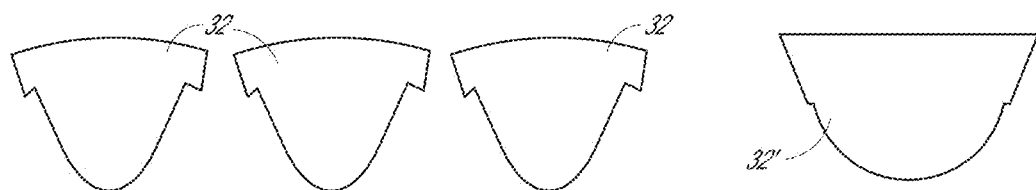
FIGS. 6 and 6A show valve leaflets configured in accordance with one embodiment.
Figure 6A:
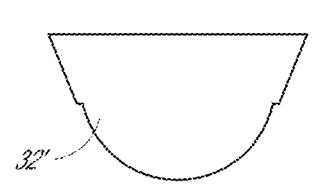

With particular reference next to FIG. 6, an embodiment of conical valve leaflet 32 is shown. This figure shows one embodiment of a pattern for cutting the leaflets 32 from a flat, tissue material such as pericardium. Preferably, upstream portions of the leaflets are generally curved and commissures are disposed along downstream side edges of the leaflets. The curvature and size of the pattern cuts, and particularly the curvature of the side edges, is chosen so that the valve fits within the generally conical shape defined by the frame 20. In the illustrated embodiment, the side edges at and adjacent the downstream end are angled relative to a longitudinal axis of the valve. As such, the valve as defined by the leaflets 32 has an outflow diameter that is greater than its inflow diameter. In addition, as discussed previously, the leaflets can extend between different diameter sections of the valve body, thus the leaflets are generally positioned at a smaller diameter at the upstream end than at the downstream end. FIG. 6A shows another embodiment of a conical leaflet pattern 32'.

Figure 7:
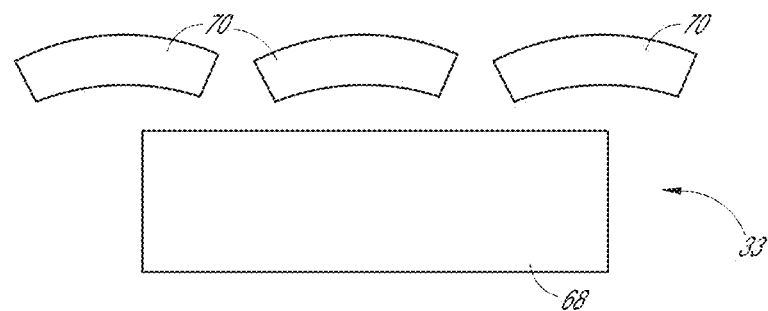
FIG. 7 illustrates components of an outer valve skirt configured in accordance with one embodiment.

In the illustrated embodiments, the outer valve skirt 33 is attached to the frame 20 and the leaflets 32 are attached to the outer valve skirt 33. Preferably, the outer valve skirt 33 is also formed of a pericardium tissue similar to the leaflets 32. The outer valve skirt 33 can be constructed in multiple different ways. For example, with reference next to FIGS. 7 and 8, embodiments show that an outer valve skirt 33, 33' can be made by cutting multiple pieces of flat tissue material and sewing the tissue together to form the outer valve skirt with the flared transition portion. In FIG. 7, a generally rectangular piece 68 makes up the constant-diameter upstream portion 38 of the outer valve skirt 33, and three or more curving pieces 70 that can be sewn together to approximate the shape of the flared transition portion 40 are cut, sewn together, and sewn to the downstream end of the upstream portion 38 to construct the outer valve skirt 33.

Figure 8:
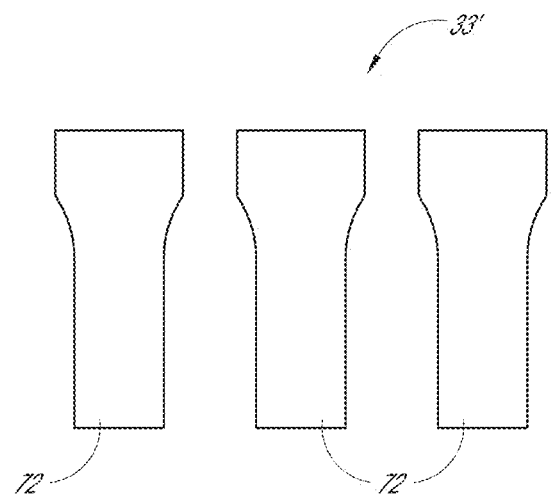
FIG. 8 illustrates components of another embodiment of an outer valve skirt.

In FIG. 8, multiple pieces 72, each having a constant-width upstream portion, an expanding-width transition portion, and a constant-width downstream portion can be employed to form an outer valve skirt 33'. In the illustrated embodiment, three such pieces are shown and can be sewn together to create the flared valve skirt. However, it is to be understood that in other embodiments, six, nine, or 12 pieces, or even other numbers of pieces can be employed to construct a flared outer valve skirt 33'.

Figure 9:
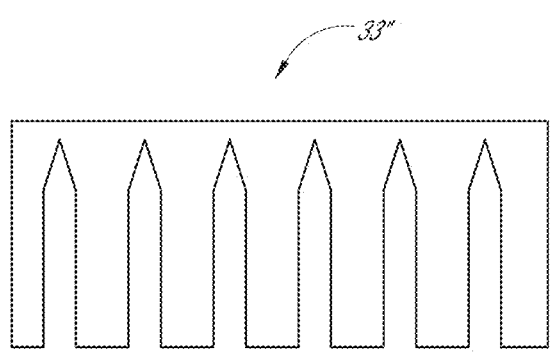
FIG. 9 illustrates components of still another embodiment of an outer valve skirt.

With reference next to FIG. 9, an embodiment of a pattern for forming an outer valve skirt 33" out of a single piece of flat tissue is shown. In this embodiment, the downstream end is generally contiguous, but cavities are cut from an upstream end down to a point adjacent the downstream end. Upstream portions of the cavities are generally constant in width so as to approximate the upstream portion of the outer valve skirt 33", and transition portions of the pattern progressively reduce in width until forming a point so as to correspond to the transition portion. In constructing the outer valve skirt 33", the opposing edges of the cavities are sewn together so that the valve skirt takes on the flared shape generally corresponding to the frame 20. In the illustrated embodiment, six cavities are used. However, in other embodiments, more or less cavities such as three, nine, or 12, can be employed.

Preferably, the outer valve skirt 33 is constructed of a tissue that is flexible, but not particularly expansive and stretchy. As such, in the illustrated embodiments, the outer valve skirt 33 extends through the non-foreshortening zone 52 of the frame 20, but does not extend into the foreshortening zone 54 of the frame 20. However, in other embodiments, a portion of the outer valve skirt 33 may extend into the foreshortening zone 54.

Referring back to FIGS. 1 and 2, in a preferred embodiment a downstream end of the outer valve skirt 33 is sewn to a connection skirt 50. The connection skirt 50 can be made of knit polyester or another stretchable fabric. The connection skirt 50 can be made to move with the foreshortening portion 54 of the frame 20.

Figure 10:
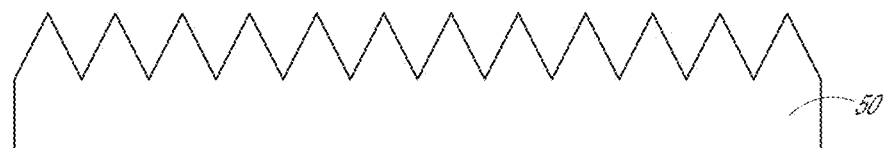
FIG. 10 shows an embodiment of a connection skirt.

With additional reference next to FIG. 10, one embodiment of a flat pattern for a connection skirt 50 is illustrated. In this embodiment, an upstream edge of the connection skirt 50 is generally straight so as to correspond to the downstream edge of the outer valve skirt 33 and contribute to an advantageous seam structure. A downstream end of the connection skirt, 50 however, undulates. Preferably, the undulations are patterned to generally correspond to undulations of struts in the foreshortening zone 24 of the frame 20, such as struts of the fifth ring 66. The undulations can match the curvature of the struts, and the connection skirt 50 is sewn along the edges of its undulations to the corresponding foreshortening cell struts, as shown in FIGS. 1 and 2. It is to be understood that other configurations of connection skirts 50 can be employed. For example, a connection skirt 50 can have a generally straight downstream end or can have undulations that do not correspond with the end 16 of the frame 20.

Figure 11:
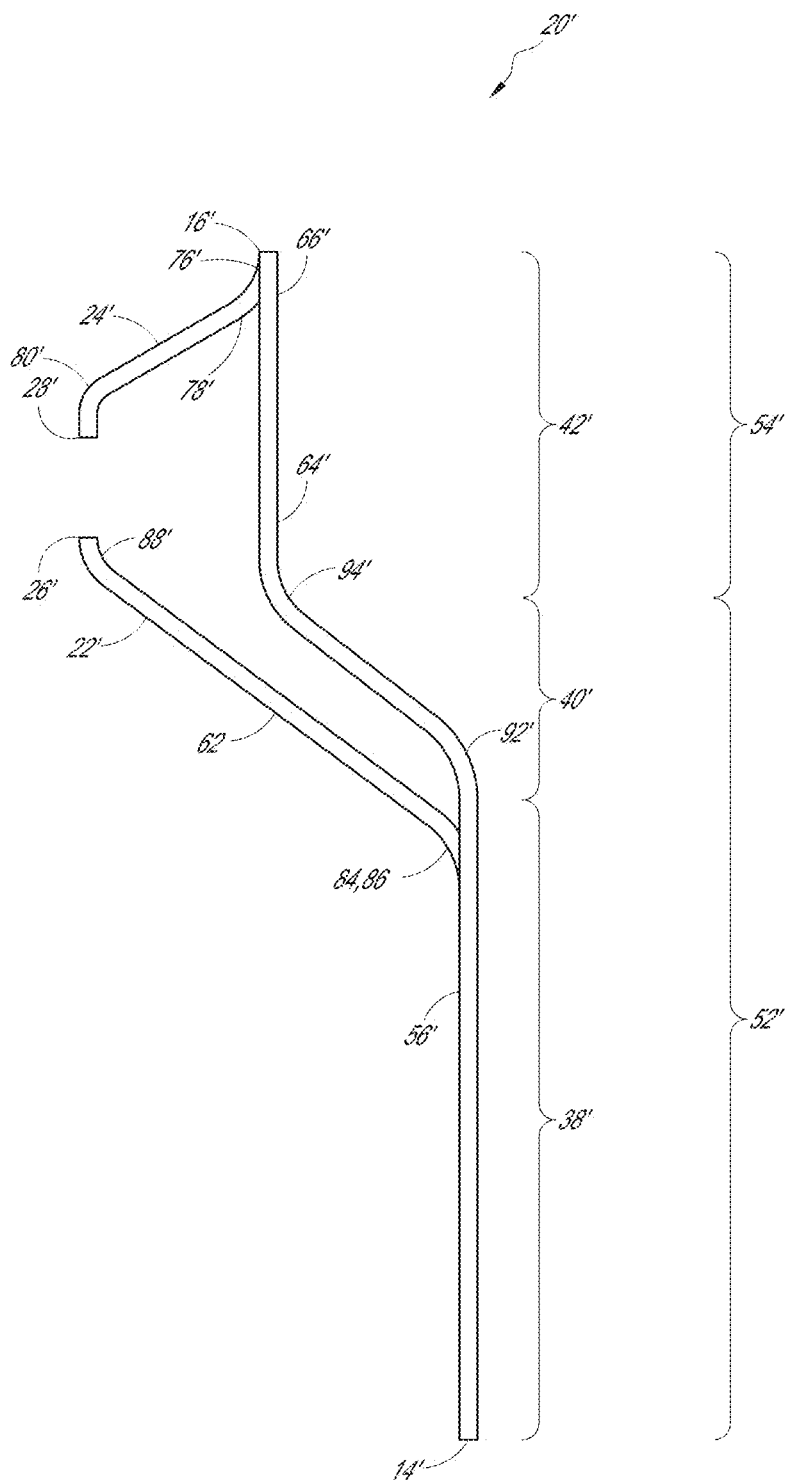
FIG. 11 is a schematic side view of another embodiment of a frame.
Figure 12:
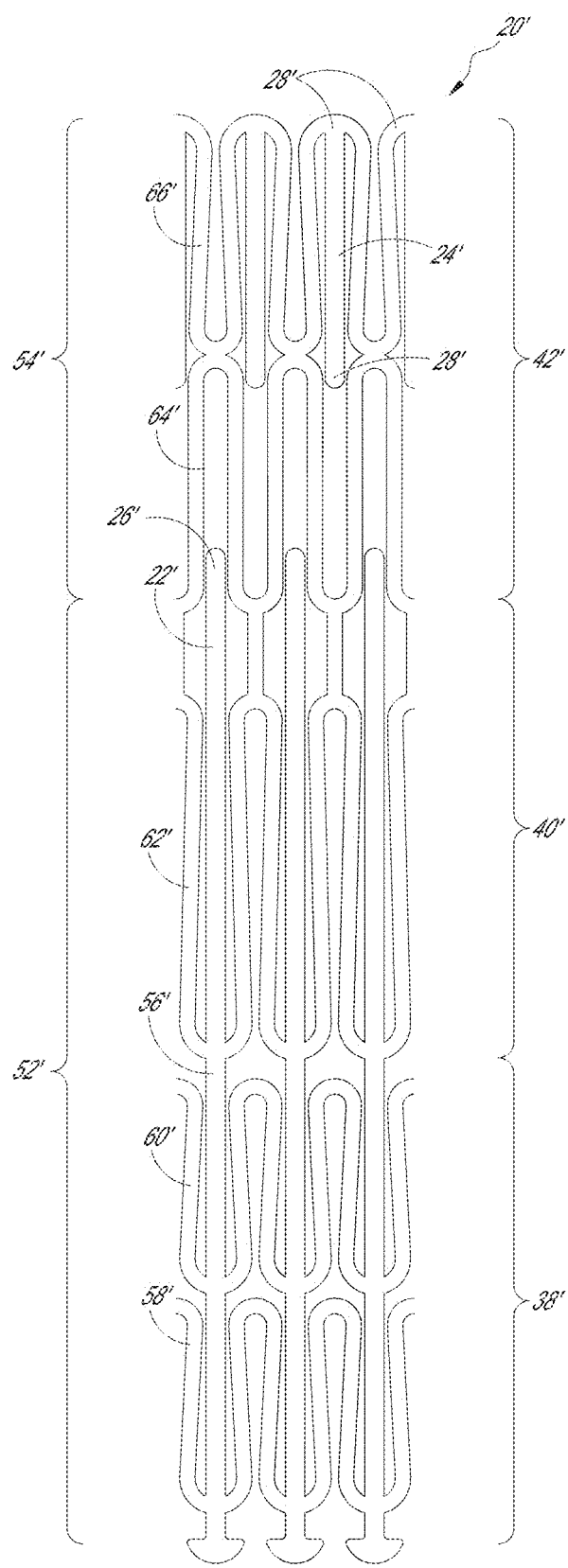
FIG. 12 is a partial flat pattern depiction of the pattern from which the frame of FIG. 11 is cut.

With reference next to FIGS. 11 and 12, a schematic side section view and flat pattern cutout view of a frame 20' in accordance with another embodiment is shown. As with the embodiment in FIGS. 1-5, the illustrated frame 20' has an upstream portion 38' of generally constant diameter, a transition portion 40' of expanding diameter and a downstream or annulus-engagement portion 42' of generally constant diameter, which diameter is greater than the upstream portion diameter. In this embodiment, longitudinal struts 56' extend distally beyond the transition portion 40', and define the upstream anchors 22'. More specifically, the longitudinal struts 56' bend radially outwardly from the upstream portion 38' upstream of the transition portion 40', and extend downstream beyond the transition portion 40' so that a downstream tip of each strut defines an anchor tip 26'. The transition portion 40' in this embodiment is made up of the undulating struts in the third ring 62'. The transition portion

40' also includes two bending stages 92', 94'. Downstream apices in the third ring 62' have second longitudinal struts 74 extending therefrom, which connect each downstream apex to an apex of closed foreshortening cells defined by the fourth 64' and fifth 66' rings.

The anchor 24' is shown with a base 76' connected to the fifth ring 66'. The anchor 24' includes first 78' and second 80' bending stages. The first bending stage 78' positions the anchor 24' away from the frame 20' and the second bending stage 80' positions the tip 28'. The anchor 22' also has first 86' and second 88' bending stages. The first bending stage 86' is located at and near the base 84' and positions the anchor 22' away from frame 20'. The second bending stage 88' positions the anchor tip 26' towards the opposing anchor 24' and positions the tip parallel or substantially parallel to the frame 20'.

In the frame 20' embodiment of FIGS. 11 and 12, since the third ring 62' is attached to the longitudinal struts 56' only at the upstream apices, at least some foreshortening can be anticipated in the transition portion 40' due to expansion of the third ring struts. In a preferred embodiment, a greater proportion of foreshortening takes place in the closed foreshortening cells of the downstream fourth 64' and fifth 66' rings than in the third ring 62'. In some embodiments, a greater proportion of the outer valve skirt or all of the outer valve skirt can be constructed of flexible fabric so that the outer valve skirt can accommodate and move with the foreshortening third ring 62', while the leaflets can continue to be made of a generally nonelastic material such as pericardium. In further embodiments, a pericardium outer valve skirt can be relatively-loosely stitched or otherwise attached to a connection skirt and the frame 20' along, for example, the second longitudinal struts 74 so that during the radial expansion process, the distal end of the outer valve skirt can move relative to the frame 20' so that the outer valve skirt and the leaflets maintain optimal geometry and placement as the frame length changes. In still further embodiments, the struts of a third ring 62' can be configured so that any foreshortening during radial expansion is sufficiently minor or small so as to not substantially affect tissue-based valve members such as the outer valve skirt and/or leaflets.

Figure 13:
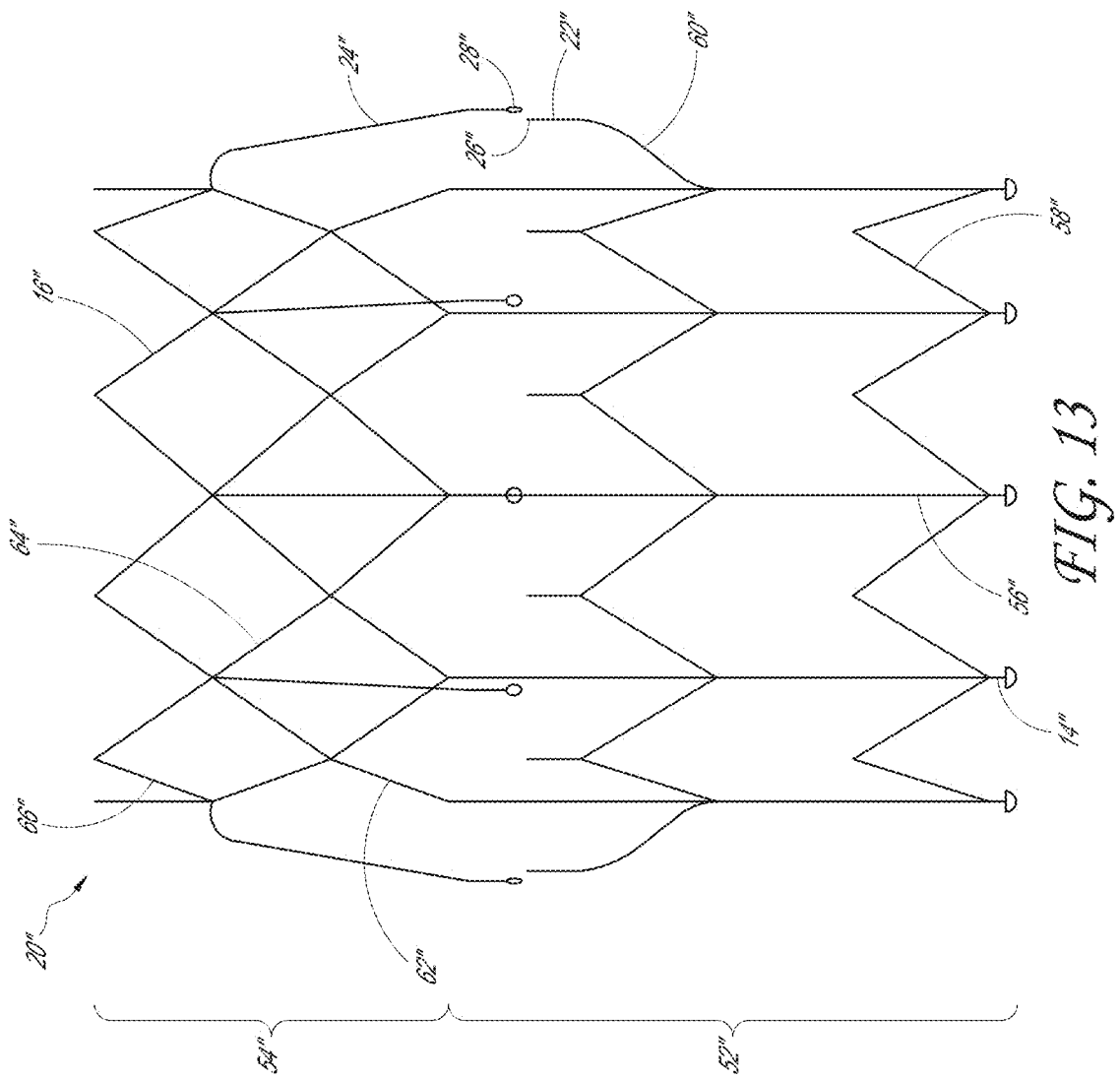
FIG. 13 is a side view of still another embodiment of a frame.

FIG. 13 shows yet another embodiment of a frame 20". The frame 20" has a substantially constant inner diameter, such that the diameter is substantially the same at the two opposing ends 14" and 16". This embodiment employs longitudinal struts 56" in the non-foreshortening portion 52" and first 58" and second 60" rings of expansible struts connected to the longitudinal struts 56". The second rings 60" flare radially outwardly as part of the anchors 22". The foreshortening zone 54" has two rows of closed foreshortening cells made by third 62", fourth 64" and fifth 66" rings. The downstream anchors 24" extend from points adjacent the downstream end 16" of the frame 20", but portions of some of the foreshortening cells are downstream of the anchor bases. In the illustrated embodiment, the downstream anchors are longer than the upstream anchors.

Figure 14:
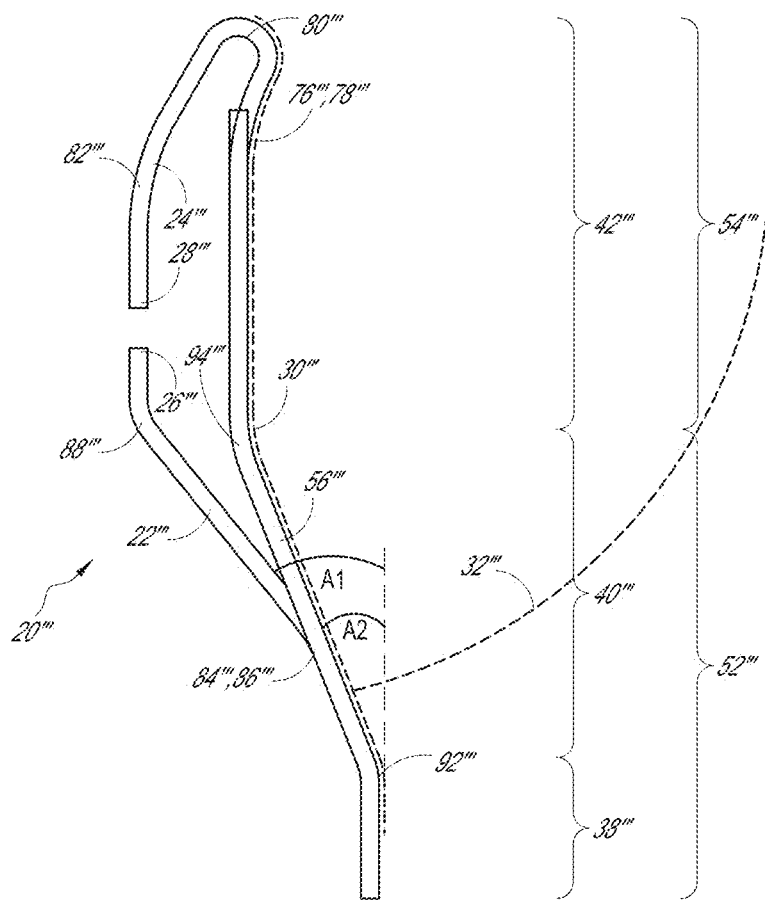
FIG. 14 shows a schematic side view of yet another embodiment of a frame.

Referring to FIG. 14, a schematic side view of a frame 20''' is shown. As mentioned previously, the frame 20 has a non-foreshortening zone 52''' and a foreshortening zone 54'''. Longitudinal struts 56''' span all or part of the length of the non-foreshortening zone 52'''. Distal or downstream portions of the longitudinal struts 56''' make up all or part of the transition portion 40''', in which the struts 56''' bend at bending stage 92''' so as to flare radially outwardly and then bend again at bending stage 94''' so as to stop expanding in radius and attach to the foreshortening zone 54''' of the frame 20'''. As such, the frame 20''' is generally divided into an upstream portion 38''' made up of the first diameter, a transition portion 40''' at which the diameter is expanding, and a downstream portion 42''' which includes the foreshortening zone 54''' and which is adapted to engage the native valve annulus.

One, two, three, or more rings made up of undulating struts can be connected to the longitudinal struts 56''' in the non-foreshortening zone 52'''. One, two, three, or more rings made up of undulating struts can also be used to form the foreshortening zone 54'''.

Downstream anchors 24''' can extend from a portion of the downstream portion 42''' or foreshortening portion 54''' as shown. The downstream anchors 24''' are bent down or bent out from the frame 20''' and flared radially out from the frame 20'''. Anchor 24''' is shown with a base 76''' connected to the frame 20'''. The anchor 24''' includes first 78''', second 80''' and third 82''' bending stages. The first bending stage 78''' is a radially inward bend. The inward bend can be between about 5-30 degrees, for example. The second bending stage 80''' can have a large bend, such as an approximately 180 degree radially outwardly extending bend, or between around 150-200 degrees, as has been described. After the second stage bend the anchor extends in an upstream and radially outward direction. The first 78''' and second 80''' bending stages can position the anchor 24''' away from the frame 20'''. The third bending stage 82''' can position the tip 28''', such as to position the tip 28''' to oppose the anchor tip 26''' and/or position the tip 28''' parallel or substantially parallel with the frame 20'''. The bend at the third bending stage can be, for example, between about 5-30 degrees.

Upstream anchors 22''' preferably extend from the non-foreshortening portion 52'''. For example, upstream anchors 22''' and/or the ring(s) or struts to which they are attached, are shown extending from the transition portion 40'''. As can be seen in FIG. 14, the upstream anchors 22''' are flared radially out at a more dramatic angle than is the longitudinal strut 56'''. As has been mentioned above, the transition portion 40''' has a first bending stage 92''' and a second bending stage 94''' which changes the diameter of the frame 20''' between the upstream portion 38''' and the downstream portion 42'''. The anchor 22''' also has first 86''' and second 88''' bending stages. The first bending stage 86''' is located near or at the base 84''' and directs the anchor 22''' away from frame 20'''. The second bending stage 88''' directs the anchor tip 26''' towards the opposing anchor 24''' and preferably positions the tip parallel or substantially parallel to the frame 20'''.

In this embodiment, the anchors 22''' extend from the frame 20''' at the transition portion 40''' rather than at the upstream portion 38'''. This allows the anchors 22''' to have a smaller bend or angle at the first bending stage 86''' because some of the desired bend is already provided by the first bending stage 92''' of the transition at portion 40'''. For example, where it is desired to position the anchor 22''' an angle $A_1$ from the upstream portion, the first bending stage 92''' of the transition portion 40''' can be bent an angle $A_2$ and then the first bending stage 86''' of the anchor 22''' can be bent the remaining amount to provide the angle $A_1$. For example, where the anchor 22''' is positioned an angle $A_1$ of approximately 40 degrees from the frame of the upstream portion 38''', the transition portion can be positioned at an angle $A_2$ of approximately 20 degrees or 30 degrees and then the anchor 22 can be positioned an additional amount from frame at the transition portion to make up the entire 40 degrees.

In another embodiment, the anchor 22''' can extend from the upstream portion of the frame, and can have a first bending stage at which the anchor bends approximately the same as the first bending stage of the transition portion. The anchor 22''' can have a second bending stage spaced from the first stage and which directs the anchor 22''' further radially outwardly to the desired angle $A_1$. The anchor 22''' has a third bending stage to position the anchor tip 26'''.

The upstream anchors 22''' are bent so as to generally oppose the downstream anchors 24''' that extend from the foreshortening zone 54'''. A tip 26''' of each upstream anchor 22''' is downstream of the transition portion 40'''. As such, the anchor tips 26, 28 of the opposing anchors 22, 24 can be disposed on opposite sides of the native annulus of a heart valve and used to engage the valve to thereby replace the valve with a replacement heart valve as has been described herein.

As can also be seen in FIG. 14, the valve body 30''' can be attached to the frame 20'''. The valve body 30''' can be positioned in the upstream 38''', transition 40''', and/or downstream 42''' portions. The valve body 30''' can also be positioned in both the foreshortening 54''' and the non-foreshortening 52''' zones. An example leaflet 32''' is also illustrated. In this embodiment, the leaflet 32''' is within the transition portion 40''' and the downstream portion 42''' but is not within the upstream portion 38'''.

In some embodiments, the implant can be delivered via a transvenous, transseptal, or an antegrade approach.

Figure 15:
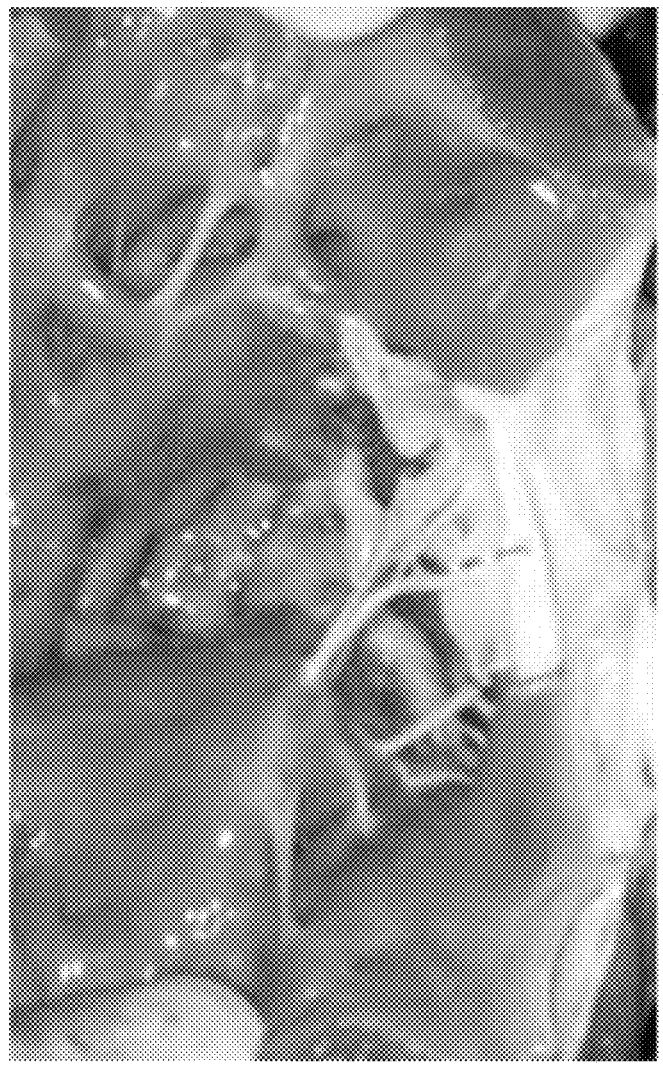
FIGS. 15-19 are photographs filed in U.S. Provisional Application No. 61/357,048, filed on Jun. 21, 2010, which has been incorporated herein by reference.
Figure 16:
Figure 17:
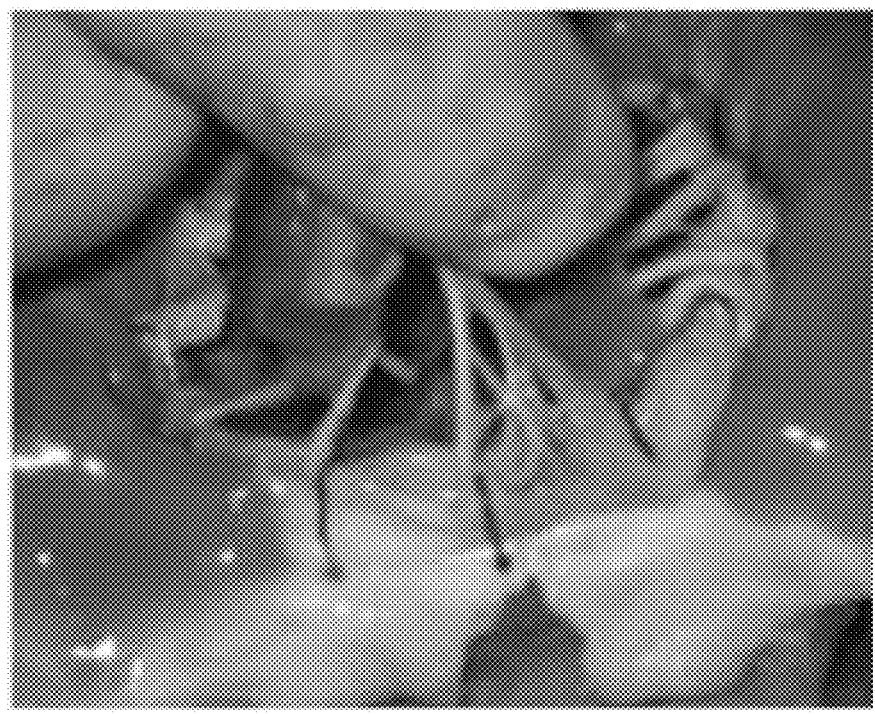
Figure 18:
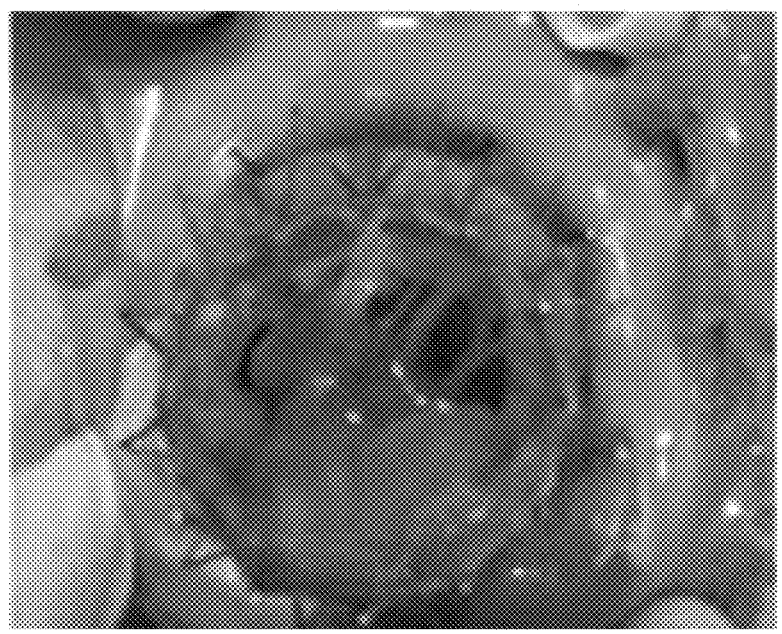
Figure 19:
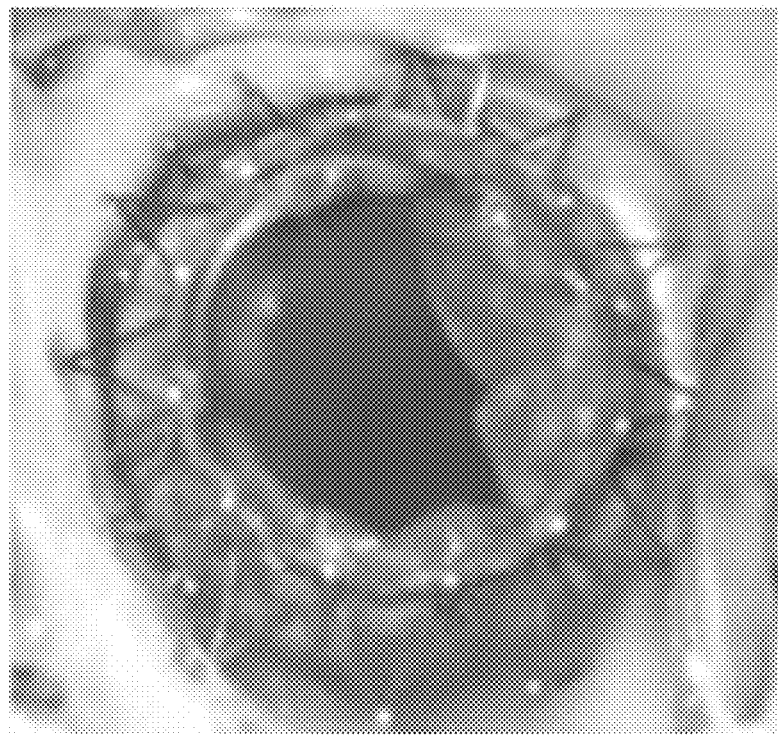

FIGS. 15-19 are photographs filed in U.S. Provisional Application No. 61/357,048, filed on Jun. 21, 2010, which has been incorporated herein by reference. These images are of post-implant examination which showed engagement of an implant with native leaflets and annulus. Referring next to FIGS. 15-19, an embodiment of a valve 10'''' having a frame 20'''' and valve body 30'''' is shown deployed within a native mitral valve. FIGS. 15-17 are shown from within the left ventricle and FIGS. 18 and 19 are shown from within the left atrium.

With reference first to FIGS. 15-17, the downstream anchors 24'''' can extend around the native mitral valve leaflets. As shown, the downstream anchors 24'''' extend between chordae tendineae coupling the native mitral valve leaflet and papillary heads of papillary muscle. The tips 28'''' of the downstream anchors 24'''' can engage the native mitral valve annulus. As shown in the illustrated embodiment, in some instances tips 28'''' of the downstream anchors 24'''' can engage the fibrous trigones of the native mitral valve. With reference next to FIGS. 18 and 19, the tips 26'''' of the upstream anchors 22'''' can engage the native mitral valve annulus.

What is claimed is:

1. A method of delivering a replacement valve to a native mitral valve of a heart and securing the replacement valve relative to a native mitral valve annulus, the native mitral valve positioned between a left atrium and a left ventricle, the method comprising:
   delivering the replacement valve to the native mitral valve annulus while the replacement valve is in a radially compacted state, the replacement valve comprising:
      an expandable frame having a proximal end ending at a proximalmost end and a distal end ending at a distalmost end;
      a valve body positioned within a lumen of the expandable frame; and
      one or more distal anchors extending from the distal end of the expandable frame and sized to contact tissue on a ventricular side of the native mitral valve when the replacement valve is deployed within the native mitral valve; and
   deploying the replacement valve within the native mitral valve annulus such that:
      the replacement valve is in an expanded configuration with a cross-sectional diameter of the distalmost end of the expandable frame being greater than a cross-sectional diameter of the proximalmost end of the expandable frame, the replacement valve only decreasing or remaining constant in cross-sectional diameter from the distalmost end to the proximalmost end;
      the one or more distal anchors are positioned radially outwardly from the frame;
      tips of the one or more distal anchors extend substantially parallel to a longitudinal axis of the expandable frame; and
      at least one of the distal anchors extends between chordae tendineae of the native mitral valve.

2. The method of claim 1, wherein:
   the expandable frame further comprises a proximal anchoring portion sized to contact tissue on an atrial side of the native mitral valve when the replacement valve is deployed within the native mitral valve; and
   deploying the replacement valve within the native mitral valve annulus comprises expanding the replacement valve such that the proximal anchoring portion is positioned radially outwardly from the frame.

3. The method of claim 2, wherein the proximal anchoring portion comprises a plurality of free apices each connected to the expandable frame at a first base and at a second base, the first and the second bases located distal of the proximal end of the expandable frame.

4. The method of claim 2, wherein each distal anchor extends from a portion of the expandable frame having a greater cross-sectional diameter than a portion from which the proximal anchoring portion extends.

5. The method of claim 1, wherein deploying the replacement valve within the native mitral valve annulus comprises engaging at least a first of the one or more distal anchors with a first fibrous trigone of the native mitral valve.

6. The method of claim 5, wherein deploying the replacement valve within the native mitral valve annulus comprises disposing a native leaflet of the native mitral valve between at least the first distal anchor and the expandable frame.

7. The method of claim 5, wherein deploying the replacement valve within the native mitral valve annulus comprises engaging at least a second of the one or more distal anchors with the native mitral valve annulus.

8. The method of claim 1, wherein delivering the replacement valve to the native mitral valve annulus while the replacement valve is in the radially compacted state comprises delivering the replacement valve from a region outside the heart to the left ventricle of the heart.

9. The method of claim 8, wherein delivering the replacement valve to the native mitral valve annulus while the replacement valve is in the radially compacted state comprises transseptally delivering the replacement valve.

10. The method of claim 1, wherein the expandable frame further comprises an engagement zone, and wherein expanding the replacement valve comprises radially expanding the engagement zone of the expandable frame to engage the native mitral valve annulus.

11. The method of claim 1, wherein the valve body comprises a plurality of valve leaflets.

12. The method of claim 11, wherein the replacement valve comprises a plurality of commissures disposed along downstream side edges of the valve leaflets.

13. The method of claim 11, wherein the valve body comprises three leaflets.

14. The method of claim 11, wherein the plurality of valve leaflets are configured to open to allow flow in a first direction from the left atrium to the left ventricle and engage one another so as to close and not allow flow in a second direction opposite the first direction.

15. The method of claim 1, wherein each of the one or more distal anchors is formed by a single strut.

16. The method of claim 1, wherein the tips of the one or more distal anchors are enlarged relative to a remainder of the one or more distal anchors to increase a surface area of the tips in contact with the tissue on the ventricular side of the native mitral valve when the replacement valve is expanded and deployed within the native mitral valve.

17. The method of claim 1, wherein the expandable frame comprises a plurality of cells, and wherein the valve body is fully located radially within the plurality of cells of the expandable frame.

\* \* \* \* \*